US011638557B2

(12) United States Patent
Lee et al.

(10) Patent No.: US 11,638,557 B2
(45) Date of Patent: *May 2, 2023

(54) DETECTION AND CALCULATION OF HEART RATE RECOVERY IN NON-CLINICAL SETTINGS

(71) Applicant: Intel Corporation, Santa Clara, CA (US)

(72) Inventors: Jonathan K. Lee, San Francisco, CA (US); Marco Della Torre, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 815 days.

This patent is subject to a terminal disclaimer.

(21) Appl. No.: 16/530,130

(22) Filed: Aug. 2, 2019

(65) Prior Publication Data

US 2020/0163619 A1     May 28, 2020

Related U.S. Application Data

(63) Continuation of application No. 15/036,364, filed as application No. PCT/US2015/010003 on Jan. 1, 2015, now Pat. No. 10,420,504.

(Continued)

(51) Int. Cl.
*A61B 5/00* (2006.01)
*A61B 5/024* (2006.01)
(Continued)

(52) U.S. Cl.
CPC .......... *A61B 5/4884* (2013.01); *A61B 5/0205* (2013.01); *A61B 5/02438* (2013.01);
(Continued)

(58) Field of Classification Search
None
See application file for complete search history.

(56) References Cited

U.S. PATENT DOCUMENTS

| 4,898,182 A | 2/1990 | Hawkins et al. |
| 6,356,857 B1 | 3/2002 | Qin et al. |

(Continued)

FOREIGN PATENT DOCUMENTS

EP       2520222 A1    11/2012

OTHER PUBLICATIONS

"Autonomic contribution to heart rate recovery from exercise in humans", Savin, et al., Journal of Applied Physiology 53.6 (1982): 1572-1575.

(Continued)

*Primary Examiner* — Jacqueline Cheng
*Assistant Examiner* — Jairo H Portillo
(74) *Attorney, Agent, or Firm* — Patent Capital Group

(57) ABSTRACT

A wearable device measures heart rate recovery of a user in a non-clinical setting. The wearable device comprises a heart rate detector configured to detect heart rate data of the user, an activity sensor configured to detect motion of the user, and a processor. The processor is configured to identify a start of an activity by the user using the motion detected by the activity sensor. Responsive to detecting the start of the activity, the processor monitors the motion detected by the activity sensor to identify an end of the activity. A regression analysis is performed on heart rate data detected by the heart rate detector during a period of time after the end of the activity, and the heart rate recovery of the user is determined using the regression analysis.

20 Claims, 4 Drawing Sheets

Related U.S. Application Data

(60) Provisional application No. 61/923,182, filed on Jan. 2, 2014.

(51) Int. Cl.
*A61B 5/11* (2006.01)
*A61B 5/0205* (2006.01)

(52) U.S. Cl.
CPC .......... *A61B 5/1118* (2013.01); *A61B 5/4806* (2013.01); *A61B 5/4866* (2013.01); *A61B 5/681* (2013.01); *A61B 5/72* (2013.01); *A61B 5/112* (2013.01); *A61B 5/6824* (2013.01); *A61B 5/6887* (2013.01)

(56) References Cited

U.S. PATENT DOCUMENTS

| | | |
|---|---|---|
| 6,904,313 B1 | 6/2005 | Snell |
| 2005/0065443 A1 | 3/2005 | Ternes |
| 2007/0249949 A1 | 10/2007 | Hadley |
| 2009/0216143 A1 | 8/2009 | Tulppo et al. |
| 2011/0184296 A1 | 7/2011 | Vajdic et al. |
| 2011/0184303 A1 | 7/2011 | Skinner et al. |
| 2011/0257542 A1 | 10/2011 | Russell et al. |
| 2012/0071731 A1 | 3/2012 | Gottesman |
| 2013/0023739 A1 | 1/2013 | Russell |
| 2016/0278700 A1 | 9/2016 | Lee et al. |

OTHER PUBLICATIONS

"Real time." Merriam-Webster Online Dictionary. 2010. Merriam-Webster Online. May 20, 2019 (Year:2010).

European Search Report for Application No. 15733076.2-1657/3089659, dated Jul. 26, 2017, 8 pages.

Final Office Action in U.S. Appl. No. 15/036,364 dated Mar. 8, 2019, 31 pages.

International Preliminary Report on Patentability and Written Opinion in International Application No. PCT/US2015/010003 dated Jul. 5, 2016.

International Search Report and Written Opinion in International Application No. PCT/US2015/01003 dated Jul. 9, 2015.

Non Final Office Action in U.S. Appl. No. 15/036,364 dated Jul. 30, 2018, 29 pages.

Notice of Allowance in Chinese Patent Application No. 201580082917.8 dated May 14, 2019, 8 pages.

Notice of Allowance in U.S. Appl. No. 15/036,364 dated Jun. 6, 2019, 14 pages.

DETECTION AND CALCULATION OF HEART RATE RECOVERY IN NON-CLINICAL SETTINGS

CROSS-REFERENCE TO RELATED APPLICATION

This application is a continuation of U.S. patent application Ser. No. 15/036,364, filed on May 12, 2016 and entitled "Detection and Calculation of Heart Rate Recovery in Non-Clinical Settings" which application is a national stage application under 35 U.S.C. § 371 of PCT International Application Serial No. PCT/US2015/010003, filed on Jan. 1, 2015 and entitled "Detection and Calculation of Heart Rate Recovery in Non-Clinical Settings", which application claims the benefit of U.S. Provisional Application 61/923,182, filed Jan. 2, 2014, and entitled "Detection and Calculation of Heart Rate Recovery in Non-Clinical Settings," all of which are considered part of and are hereby incorporated by reference in their entirely in the disclosure of this application.

BACKGROUND

Heart rate recovery, the rate at which heart rate decreases immediately after exercise, is a measure of cardiovascular health and fitness. Heart rate recovery is often measured in a clinical setting by a specialist. During the clinical test, a patient walks on a treadmill at a pace controlled by the specialist to elevate the patient's heart rate, and the specialist monitors the patient's heart rate throughout the test. Because the test is completed in a controlled clinical environment, the test is inconvenient and expensive. As such, few individuals undergo heart rate recovery testing, and the test is conducted infrequently for those individuals who do undergo heart rate recovery testing. However, literature suggests that heart rate recovery improves with exercise and increased fitness. As a result, it is beneficial for a user to monitor heart rate recovery more frequently than is possible with a clinical test.

SUMMARY

A wearable device measures heart rate recovery of a user in a non-clinical setting. The wearable device comprises a heart rate detector configured to detect heart rate data of the user, an activity sensor configured to detect motion of the user, and a processor. The processor is configured to identify a start of an activity by the user using the motion detected by the activity sensor. Responsive to detecting the start of the activity, the processor monitors the motion detected by the activity sensor to identify an end of the activity. A regression analysis is performed on heart rate data detected by the heart rate detector during a period of time after the end of the activity, and the heart rate recovery of the user is determined using the regression analysis.

The wearable device for measuring heart rate recovery of a user in a non-clinical setting comprises a heart rate detector configured to detect heart rate data of the user, an activity sensor configured to detect motion of the user, and a processor configured to: identify a start of an activity by the user using the motion detected by the activity sensor; responsive to detecting the start of the activity, monitor the motion detected by the activity sensor to identify an end of the activity; perform a regression analysis on heart rate data detected by the heart rate detector during a period of time after the end of the activity; and determine the heart rate recovery of the user using the regression analysis.

The method for measuring heart rate recovery of a user in a non-clinical setting comprises identifying a start of an activity by a user using a motion detected by an activity sensor, responsive to detecting the start of the activity, monitoring the motion detected by the activity sensor to identify an end of the activity, performing a regression analysis on heart rate data detected by a heart rate detector during a period of time after the end of the activity, and determining the heart rate recovery of the user using the regression analysis.

BRIEF DESCRIPTION OF THE DRAWINGS

The disclosed embodiments have other advantages and features which will be more readily apparent from the detailed description, the appended claims, and the accompanying figures (or drawings). A brief introduction of the figures is below.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

A wearable device measures heart rate recovery of a user in a convenient manner suitable for non-clinical settings, such as home-use or ambulatory settings. The wearable device is configured to be worn by the user while exercising or throughout the user's daily activities, continuously monitoring heart rate and activity levels of the user. The device measures the user's heart rate recovery automatically, without explicit input from the user. Because the device is configured to be worn throughout daily activities, the device measures a user's heart rate recovery on a regular basis to monitor the user's physical condition and provide regular feedback as to the user's cardiovascular health.

Figure 1:
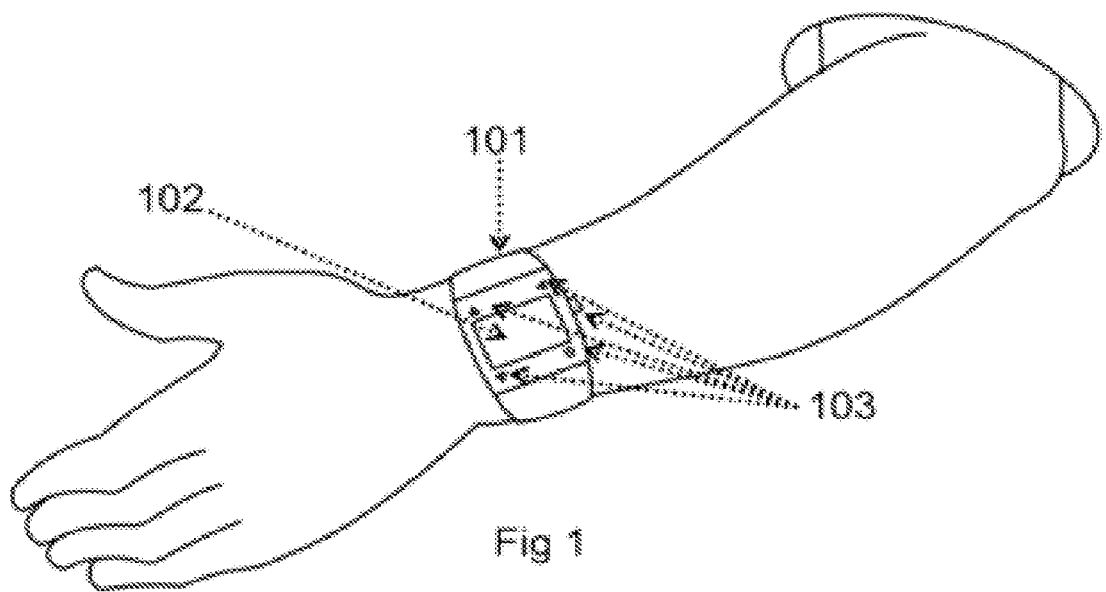
FIG. 1 illustrates a wearable device, according to one embodiment.

FIG. 1 illustrates an example of a wearable device 100. In one embodiment, the wearable device 100 is a physiological monitoring device for monitoring activities of its user and calculating various physiological and kinematic parameters, such as activity levels, caloric expenditure, step counts, heart-rate, and sleep patterns. The wearable device 100 is configured to be in close proximity to or in contact with a user. For example, the device 100 may be worn on a user's appendage or portion thereof, e.g., an arm or a wrist. As another example, the device 100 may be worn on a user's chest. A fastening system 101 configured to fasten the device 100 to a user's appendage is shown, although the device may alternatively be portable rather than worn. For example, one or more components of the device 100 may be carried in a pocket of a worn garment or affixed to a bag strap or belt. The fastening elements 101 may be removable, exchangeable, or customizable. Furthermore, although embodiments are described herein with respect to a wrist-worn device, other form factors or designed wear locations of the wearable device 100 may alternatively be used. For example, embodiments of the method described herein may be implemented in arm-worn devices, head-worn devices, chest-worn devices, clip-on devices, and so forth. Moreover, the various components of the device 100 described herein may alternatively be components of two or more devices, rather than enclosed within a single device. That is, one or more of the data collection, processing, and display functions described herein may be performed a device remote from the user. In this case, the separate components of the device 100 are communicatively coupled by wired or wireless communication, continuously communicating data between the components or transferring data at specified times. For example, a wearable component of the device 100 may continuously communicate data to an external device (e.g. a smartphone), which processes the data. As another example, a user may periodically connect a wearable component of the device 100 to an external computing device, such as a user's computer or a remote server, to transfer data collected by the wearable component to the external computer.

The wearable device 100 includes a display (or screen) 102 and several user interaction points 103. The display 102 and user interaction points 103 may be separate components of the device 100, or may be a single component. For example, the display 102 may be a touch-sensitive display configured to receive user touch inputs and display information to the user. The wearable device may also have a display element such as 102 without interaction points, or interaction points 103 without a display element such as 102.

It should be noted that the device 100 may include additional components not shown in FIG. 1. In particular, the device 100 includes one or more sensors for monitoring various physiological or kinematic parameters of the user of the device 100.

Figure 2:
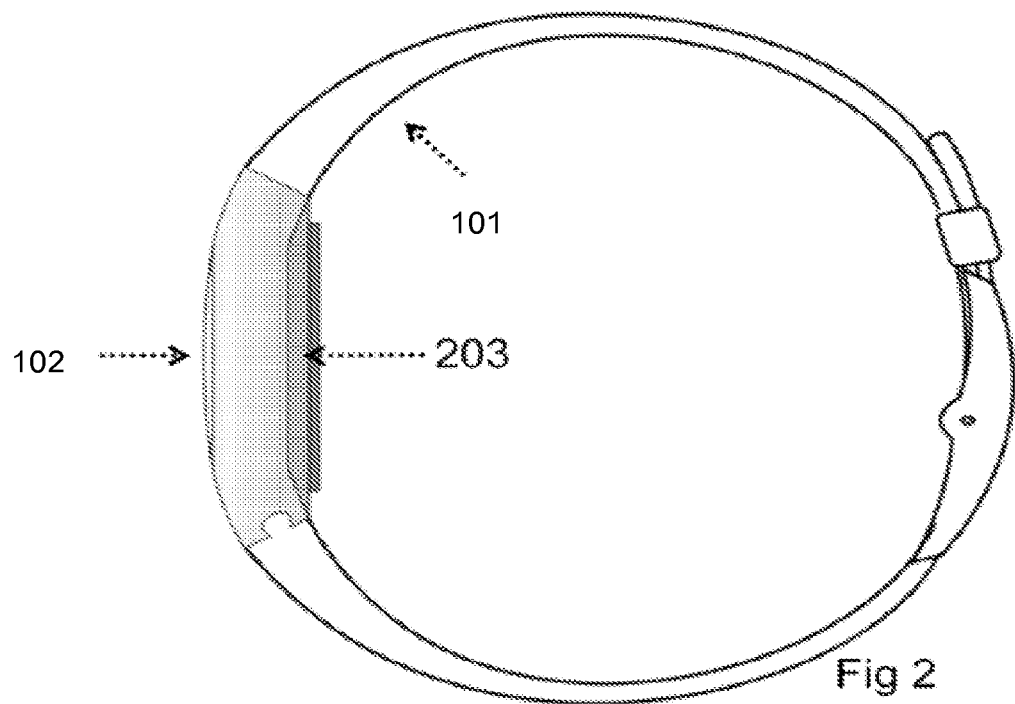
FIG. 2 illustrates an alternative view of a wearable device, according to one embodiment.

FIG. 2 is a side view of an embodiment of the device 100, showing a fastening system 101, a display (or screen) 102, and one or more processors 203. Although not shown, the device 100 may include a display driver. In addition, the device 100 also may include a memory (e.g., a random access memory (RAM) and/or read only memory (ROM)) and/or memory cache as well as a non-transitory storage medium (e.g., a flash memory). The processor 203, drivers, memories, storage medium, and sensors (further described below) may be communicatively coupled through a data bus.

Figure 3:
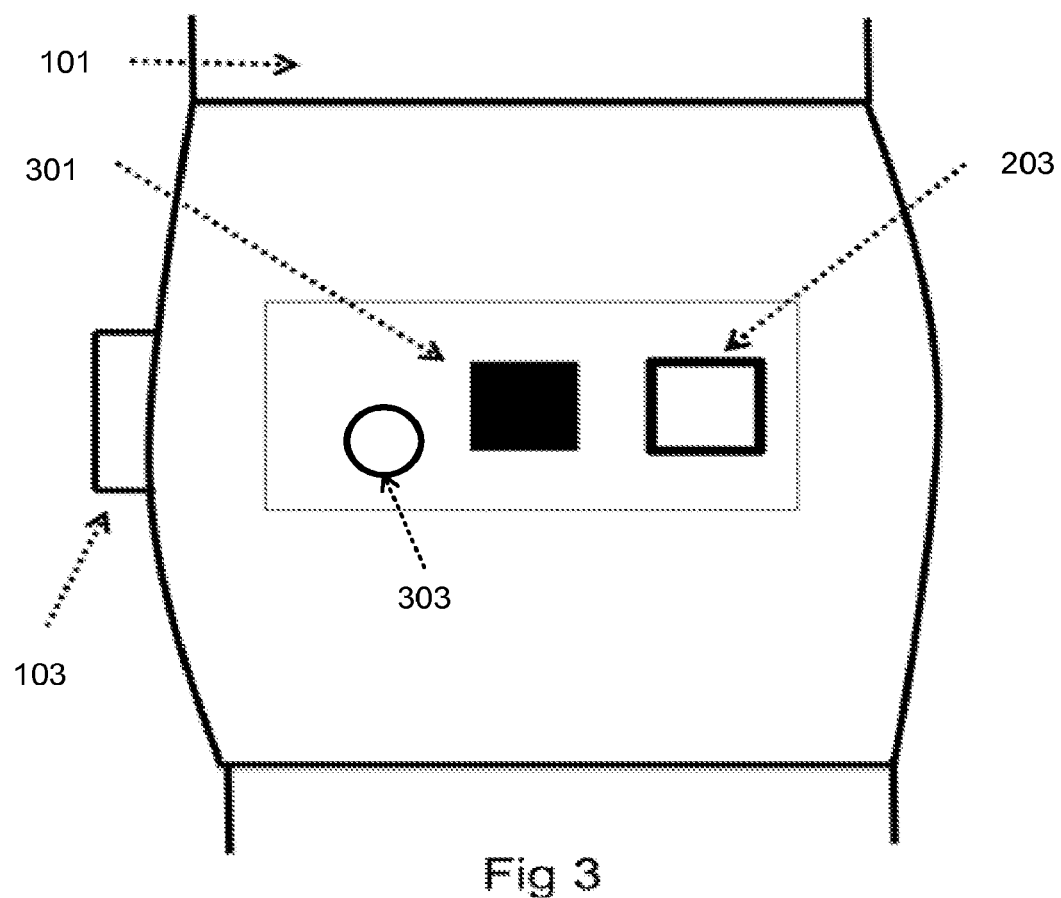
FIG. 3 illustrates another view of a wearable device, according to one embodiment.

Another view of an embodiment of the wearable device 100 is shown in FIG. 3. FIG. 3 shows a view from beneath the device 100, illustrating the fastening mechanism 101, the processor 203, a heart rate sensor 301, a motion sensor 303, and one or more user interaction points 103 visible from beneath. In other embodiments, the device 100 may include different or additional sensors, such as an electrodermal activity (EDA) sensor or other skin conductance or sweat sensor, a temperature sensor, a humidity sensor, and/or a hydration sensor.

The heart rate sensor 301 detects heart rate of a user of the device 100. In one embodiment, the heart rate sensor 301 is an optical sensor measuring a rate of blood flow. However, other types of heart rate sensors may alternatively be used, such as a tonometric pulse rate sensor, an electrocardiogram sensor, or the like. In various embodiments, the heart rate sensor 301 is communicatively coupled to the device 100, rather than being a component of the device 100. For example, the heart rate sensor 301 may be a component of a chest strap configured to be worn on the chest of a user.

The motion sensor 303 detects motion of the user of the device 100 by measuring rotational acceleration, motion, position, and/or changes in rectilinear or rotational speed of the device 100. In one embodiment, the motion sensor 303 is an accelerometer measuring acceleration of the device 100 in one or more axes. In other embodiments, the motion sensor 303 includes a gyroscope monitoring the orientation of the device 100 and/or the orientation or activity of the user. A magnetometer may be further included to calibrate the gyroscope or to provide direction-based functionality. Some embodiments of the motion sensor 303 include both an accelerometer and a gyroscope, or an accelerometer, gyroscope, and magnetometer.

The processor 203 receives data from the heart rate sensor 301 and the motion sensor 303. Using the data received from the heart rate sensor 301, the processor 203 determines heart rate of the user. In one embodiment, the processor 203 analyzes the data from the heart rate sensor 301 to determine the user's heart rate at periodic intervals, such as every ten seconds. Using the data received from the motion sensor 303, the processor 203 derives various parameters relating to the motion of the user, such as patterns in the user's movements and magnitude, frequency, and duration of the movements. The motion sensor data is used to determine an activity level of the user, which quantifies intensity of an activity based on the detected magnitude and duration. In one embodiment, the processor 203 is configured to identify a type of activity in which the user is engaged based on the data received from the motion sensor 303. For example, the processor 203 identifies if a user is walking or running based on patterns in the user's movement derived from the motion sensor data. A process for identifying activities in which the user is engaged is described in U.S. Provisional Patent Application No. 61/899,848, filed Nov. 4, 2013, which is incorporated herein by reference in its entirety. In one embodiment, the processor 203 is configured to modify the device 100 based on the detected activity. For example, a process for modifying a display of a wearable device based on a user's activity is described in U.S. Provisional Patent Application No. 61/727,074, filed Nov. 15, 2012, which is incorporated herein by reference in its entirety.

Using the motion data and heart rate, the processor 203 executes an algorithm to measure heart rate recovery of a user of the device 100. The processor 203 may automatically execute the heart rate recovery algorithm in response to detecting a sequence of events emulating a clinical heart rate recovery test, without the user of the device 100 explicitly providing input to execute the algorithm. In particular, the processor 203 executes the heart rate recovery algorithm in response to detecting a sudden decrease in the user's activity level and a low motion recovery period following a period of time in which the user's activity level was above a threshold. It is noted that the algorithms are embodied as instructions that are stored within the storage medium and/or ROM, are loadable into the memory (e.g., RAM), and are executable by the processor 203.

Figure 4:
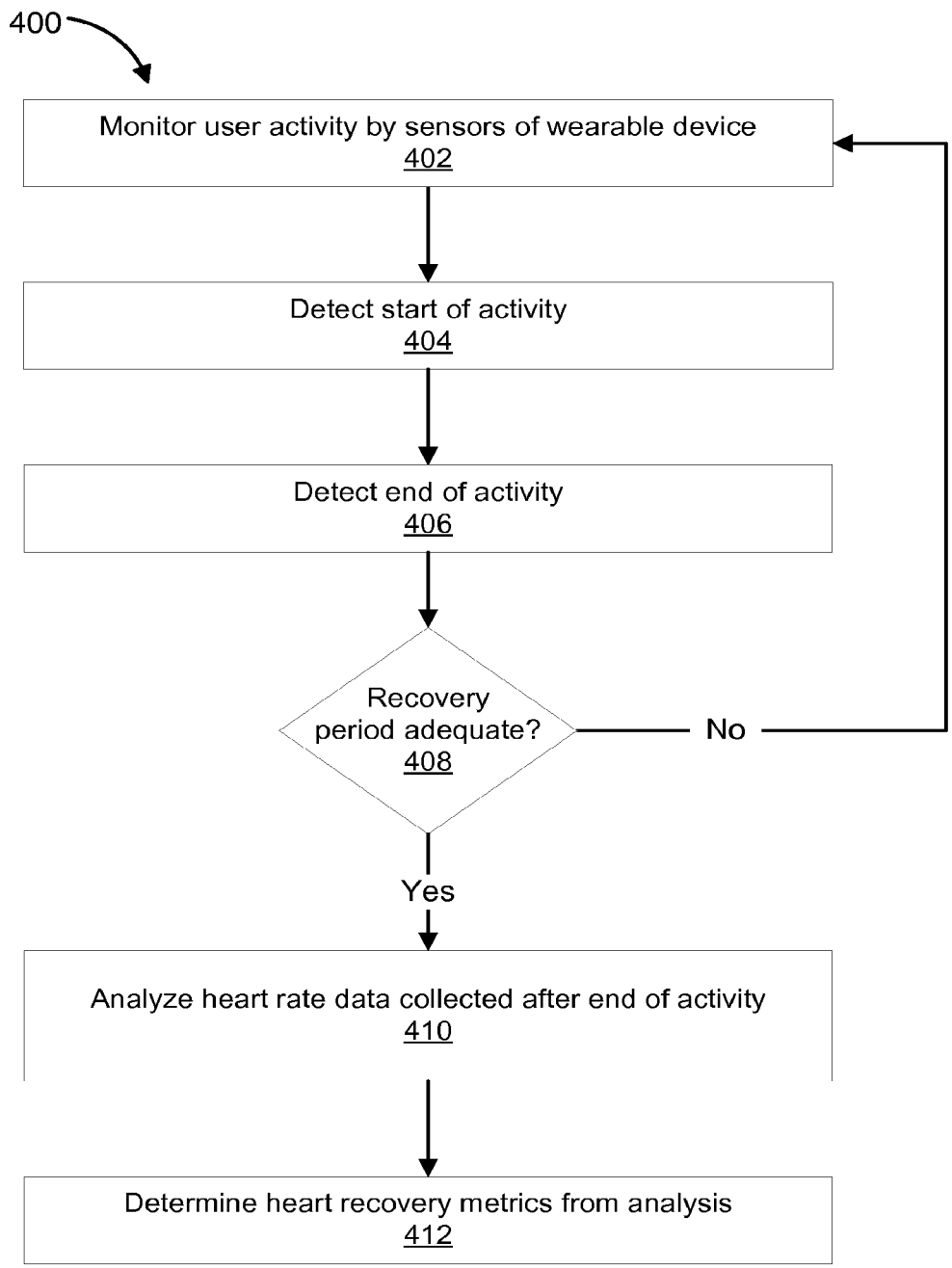
FIG. 4 is a flowchart illustrating a process for measuring heart rate recovery of a user, according to one embodiment.

The process 400 executed by the processor 203 for calculating heart rate recovery is illustrated in FIG. 4. It is noted that the process 400 may be performed substantially in real-time, or may be performed retroactively on data collected by the device 100. For example, the processor 203 may perform the process 400 once per day by analyzing data collected over the course of the day. The process 400 is discussed with reference to FIG. 5, which illustrates an example set of data collected by the processor 203 during the process 400. It is noted that the processes can be embodied as instructions that are stored within the storage medium and/or ROM, are loadable into the memory (e.g., RAM), and are executable by the processor 203.

Continuing on, the processor 203 monitors 402 user activity by sensors of the device 100, and detects 404 when the user starts an activity. In one embodiment, the processor 203 monitors 402 the activities using the motion sensor 303 to detect increases in the user's activity level above an activity threshold. An activity threshold may be a threshold magnitude or duration of sustained activity, and the time at which the activity level increases above the activity threshold is identified as the start time of the activity. In one embodiment, the processor 203 uses activity data from the motion sensor 303 to identify a type of activity in which the user is engaged, such as walking or running, as well as a time at which the user started the activity of that type. If the user activity does not exceed the activity threshold, the processor 203 continues to monitor 402 the user activity until the threshold is met. After the processor 203 has detected 404 a start of an activity, the processor 203 monitors the user activity data to detect 406 an end of the activity. In one embodiment, the detected activity end is a time at which the user's activity level falls below the activity threshold.

By monitoring the user activity using the motion sensor 303, the processor 203 determines precisely when the user begins and stops an activity. However, in other embodiments, the processor 203 monitors 402 user activities indirectly using other sensors of the device 100, such as the heart rate sensor 301 or an EDA sensor. For example, the processor 203 detects 404 the start of an activity using the user's heart rate. The time at which the user's heart rate exceeds a threshold value is identified as a time at which the user started an activity. The heart rate threshold may be a preset value or a minimum increase above the user's resting heart rate. Alternatively, the heart rate threshold may be a target heart rate, expressed as a percentage of the user's maximum heart rate as determined according to the user's weight and age. Similarly, the processor 203 detects 406 an end of the activity when the user's heart rate falls below a predefined threshold.

Figure 5:
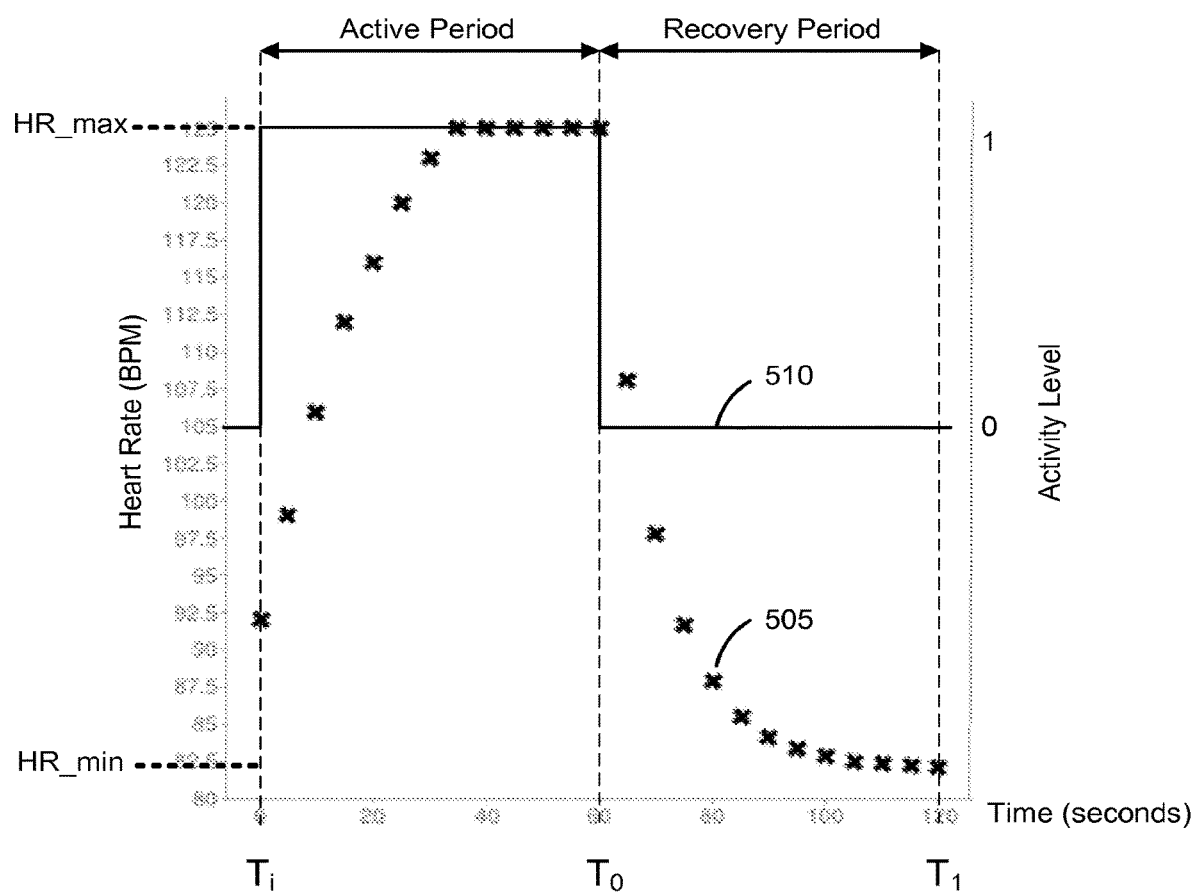
FIG. 5 illustrates an example data set collected for measuring heart rate recovery, according to one embodiment.

An example set of heart rate data 505 and activity data 510 collected by the processor 203 is shown in FIG. 5. For simplicity, the user's activity is illustrated in FIG. 5 as a binary activity level value in which the activity level is a value of 1 while the user's activity is above the activity threshold and is a value of 0 when the user's activity is below the activity threshold. Each heart rate data point shown in FIG. 5 is a sample of the user's heart rate, and is generated by the processor 203 by periodic analysis of the data from the heart rate sensor 301. At time the user begins an activity. In response to the activity, the user's heart rate increases before leveling off at an elevated value. At time $T_0$, the user ceases the activity, and the user's heart rate begins to decrease. The period of time after $T_0$ is a "recovery period," in which the user's heart recovers from an elevated heart rate of the active period. In some embodiments, the recovery period is a fixed length of time, such as 30 or 60 seconds.

The processor determines 408 whether the period of time after the end of the activity (that is, after $T_0$) is an adequate recovery period for assessing the user's heart rate recovery. A recovery period that is adequate for assessing heart rate recovery is one in which physiologically relevant heart recovery parameters can be derived from data collected during the recovery period. To determine 408 whether the interval following the end of the activity is a recovery period adequate for measuring the user's heart rate recovery, the processor 203 may analyze several factors, such as the length of time the user's activity level was above the activity threshold, the number of heart rate data points collected during a specified interval of the recovery period, how quickly the user's activity level decreased, and whether the user's activity level remained below the activity threshold for a sufficient length of time. For example, the processor 203 determines a recovery period to be adequate if the activity level was above the activity threshold for at least a threshold length of time, but determines the recovery period is not adequate for measuring heart rate recovery if the active period is shorter than the threshold length of time. As another example, the processor 203 determines that the recovery period is not adequate for measuring heart rate if the user resumes an activity above the activity threshold before a specified length of time has passed. If the recovery period is inadequate for measuring heart rate recovery, the processor 203 resumes monitoring 402 the user's activity level to detect 404 the beginning of another activity.

If the recovery period is adequate for measuring heart rate recovery, the processor 203 analyzes 410 the heart rate data collected during the recovery period. In one embodiment, the processor 203 analyzes 410 the heart rate data by performing an exponential or sigmoidal regression for the heart rate data collected during the recovery period. For example, the processor 203 may determine values for coefficients A and λ to fit an equation of the format:

$$HR = Ae^{-\lambda t} \qquad (1)$$

to the heart rate data collected during the recovery period, where HR is the user's heart rate at time t. In one embodiment, the goodness of fit of the curve fitting is used to determined 408 whether the recovery period is adequate for measuring heart rate recovery. Furthermore, by fitting an equation to the heart rate samples, the processor 203 estimates the user's heart rate between samples by interpolation. For example, if one or more heart rate samples are missed during the recovery period or if the recovery period is shorter than a desired threshold length, the processor 203 estimates the missing values using the curve fit. The processor 203 may also determine the maximum heart rate HR_max and minimum heart rate HR_min measured after the cessation of activity by identifying the maximum and minimum values measured during the recovery period or a specified portion of the recovery period, or by calculating an expected maximum or minimum using the curve fit. In other embodiments, the processor 203 analyzes 410 the heart rate data using a correlation between time and heart rate, or using a gradient calculated by subtracting adjacent heart rate values. The analysis 410 may further include analyzing the intensity of the user's activity using data from the heart rate sensor 301 and/or the motion sensor 303, and analyzing environmental parameters measured by a temperature, humidity, or hydration sensor. If the recovery period is sufficiently long, the processor 203 may perform the analysis 410 on heart rate data collected within a specified portion of the recovery period, such as the first minute after the end of the activity. For example, time $T_1$ in FIG. 5 represents the end of the portion of the recovery period over which the processor 203 performs the analysis.

Using the analysis 410, the processor 203 determines 412 heart recovery metrics for the user. In one embodiment, the processor 203 uses the exponential or sigmoidal curve fitting to determine 412 the user's heart recovery metrics. For example, the value of $\lambda$ in equation (1) represents a rate of decrease of the user's heart rate during the recovery period, where a large value of $\lambda$ indicates that the user's heart rate decreases rapidly after exercise. The value of $\lambda$ is therefore output as a measurement of the user's heart rate recovery in some embodiments. In this case, the processor 203 may also output the goodness of fit of the determined curve fitting, or may use the goodness of fit to assess accuracy of the calculated heart rate recovery metric. For example, if the goodness of fit is below a threshold value, the processor 203 does not output the calculated value of 2.

In another embodiment, the processor 203 outputs the difference between HR_max and HR_min as a measure of the user's heart rate recovery. If heart rate samples are missing during the recovery period, such that HR_max and/or HR_min are not directly measured, the processor 203 calculates the expected heart rate at time $T_0$ or $T_1$ using the curve fit to estimate the value of HR_max or HR_min, respectively, and outputs the difference between the calculated HR_max and HR_min as the user's heart rate recovery. In yet another embodiment, the processor 203 outputs the amount of time for the user's heart rate to decrease by a specified amount, such as 30 beats per minute.

Each measurement of the user's heart rate recovery may be individually stored and analyzed, or the processor 203 may average several measurements of the user's heart rate recovery to improve the accuracy of the metrics. For example, the processor 203 may average measurements collected over the course of a day and output the average value as the user's heart rate recovery metric for the day. The processor 203 may equally weight the measurements when computing the average, or may weight the measurements using goodness of fit of each measurement or other data quality measures. In the latter case, measurements having a higher reliability or quality (as determined, for example, using the goodness of fit) are weighted more heavily than measurements having a lower reliability or quality, improving the accuracy of the averaged heart rate recovery metric. Other processing may also be performed on the heart rate recovery measurements. For example, the processor 203 may normalize each measurement to intensity level of the corresponding activity, environmental parameters measured by a temperature, humidity, or hydration sensor, or orientation of the user during the activity and recovery period.

The process 400 for measuring a user's heart rate recovery may be performed repeatedly for the same user to monitor the user's physical fitness over time. In one embodiment, the processor 203 continuously monitors the user's activity levels and measures the user's heart rate recovery any time sufficient activity levels and recovery periods are detected. Alternatively, the processor 203 may perform the heart rate recovery measurement process 400 at periodic intervals, such as once per week, or when a user provides an input to capture a heart rate recovery measurement.

The processor 203 may output the user's heart rate recovery metric to the display 102 of the wearable device and/or store the metric for future analysis. In one embodiment, the user's heart rate recovery metrics are periodically reported over a network to a coach, trainer, physician, physical therapist, or the like, who uses the heart rate recovery metrics to monitor the user's physical condition over a period of time. For example, an athlete's heart rate recovery may be reported to a coaching service, in which a coach uses the athlete's heart rate recovery to assess the athlete's physical condition and design workouts to improve the athlete's fitness level. As another example, a doctor may monitor the heart rate recovery of a patient at risk for heart disease to prevent or quickly diagnose any potentially dangerous conditions. Similarly, a physical therapist may monitor the heart rate recovery of a patient to quantify the effect of therapy on the patient's physical condition. Furthermore, trends in a user's fitness can be predicted using stored heart rate recovery metrics. For example, a trend can indicate whether a user is becoming more or less fit, and may be used to predict future heart rate recovery values, issue recommendations in advance of the reduction in fitness, trigger alerts to trainers or caretakers, or provide an adjusted user experience to correct any undesirable trends towards lower fitness.

The device and process described herein for measuring heart rate recovery provides convenient, cost-effective monitoring of a user's physical condition. Because the process is executed automatically, users do not need to visit a specialist or undergo a controlled clinical test. The measurement can therefore be conducted on a more frequent basis than is feasible for the clinical test. With a larger number of measurements collected, the heart rate recovery metrics generated by the process described herein provide regular feedback to users and may be less susceptible to anomalous measurements.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. For example, the functions corresponding to the process steps in FIGS. 4 and 5 may be embodied as discrete modules (e.g., one for each function). Modules may constitute either software modules (e.g., program code (or instructions) embodied on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., processor 203) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein, e.g., such as those described with FIGS. 3, 4 and 5, may be performed, at least partially, by one or more processors, e.g., 203, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for measuring heart rate recovery through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A wearable device, comprising:
  a heart rate detector configured to detect heart rate data of a user;
  an activity sensor configured to detect motion of the user; and
  a processor configured to:
    identify a start of an activity by the user using the motion detected by the activity sensor;
    monitor, responsive to detecting the start of the activity, the motion detected by the activity sensor to identify an end of the activity; and
    determine a heart rate recovery of the user in real-time based on heart rate data detected at specified intervals by the heart rate detector during a period of time after the end of the activity, and wherein the heart rate data detected at each of the specified intervals is an individual heart rate data sample.

2. The wearable device of claim 1, wherein the processor is further configured to:
    determine an activity level of the user using the motion detected by the activity sensor;
    wherein the start of the activity is identified responsive to the activity level being greater than an activity threshold; and
    wherein the end of the activity is identified responsive to the activity level decreasing below the activity threshold.

3. The wearable device of claim 2, wherein the activity threshold comprises at least one of a magnitude of the motion detected by the activity sensor and a duration of the motion detected by the activity sensor.

4. The wearable device of claim 1, wherein the processor is further configured to:
    analyze the period of time after the end of the activity to determine if the period of time is a recovery period; and
    wherein the heart rate recovery is determined responsive to the period of time after the end of the activity being a recovery period.

5. The wearable device of claim 4, wherein the processor is further configured to:
    determine if the period of time after the end of the activity is a recovery period responsive to a length of time between the start of the activity and the end of the activity being greater than a threshold.

6. The wearable device of claim 4, wherein the processor is further configured to:
    determine if the period of time after the end of the activity is a recovery period responsive to a length of the period of time after the end of the activity, where an activity level is below an activity level threshold, being greater than a duration threshold.

7. The wearable device of claim 4, wherein the processor is further configured to:
    determine if the period of time after the end of the activity is a recovery period responsive to a number of data points of the heart rate data detected during the period of time, where an activity level is below an activity level threshold, being greater than a data point threshold.

8. A system, comprising:
    a heart rate detector configured to detect heart rate data of a user; and
    a processor configured to:
        identify a start of an activity by the user using motion detected by an activity sensor;
        monitor, responsive to detecting the start of the activity, the motion detected by the activity sensor to identify an end of the activity; and
        determine a heart rate recovery of the user in real-time based on heart rate data detected at specified intervals by the heart rate detector during a period of time after the end of the activity, and wherein the heart rate data detected at each of the specified intervals is an individual heart rate data sample.

9. The system of claim 8, wherein the heart rate data is detected during an activity performed by the user, and wherein the processor is further configured to:
    analyze a period of time after an end of the activity to determine if the period of time is a recovery period; and
    wherein the heart rate recovery is determined responsive to the period of time after the end of the activity being a recovery period.

10. The system of claim 9, wherein the processor is further configured to:
    determine if the period of time after the end of the activity is a recovery period responsive to a length of time between a start of the activity and the end of the activity being greater than a threshold.

11. The system of claim 9, wherein the processor is further configured to:
    determine if the period of time after the end of the activity is a recovery period responsive to a length of the period of time after the end of the activity, where an activity level is below an activity level threshold, being greater than a duration threshold.

12. The system of claim 9, wherein the processor is further configured to:
    determine if the period of time after the end of the activity is a recovery period responsive to a number of data points of the heart rate data detected during the period of time, where an activity level is below an activity level threshold, being greater than a data point threshold.

13. A method, comprising:
    identifying a start of an activity by a user using motion detected by an activity sensor;
    monitoring, responsive to detecting the start of the activity, the motion detected by the activity sensor to identify an end of the activity; and
    determining a heart rate recovery of the user in real-time based on heart rate data detected at specified intervals by a heart rate detector during a period of time after the end of the activity, and wherein the heart rate data detected at each of the specified intervals is an individual heart rate data sample.

14. The method of claim 13 further comprising:
    determining an activity level of the user using the motion detected by the activity sensor;
    wherein the start of the activity is identified responsive to the activity level being greater than an activity threshold; and
    wherein the end of the activity is identified responsive to the activity level decreasing below the activity threshold.

15. The method of claim 14, wherein the activity threshold comprises at least one of a magnitude of the motion detected by the activity sensor and a duration of the motion detected by the activity sensor.

16. The method of claim 13, wherein the start of the activity is identified responsive to a heart rate of the user increasing above a threshold heart rate, and wherein the end of the activity is identified responsive to the heart rate of the user falling below the threshold heart rate.

17. The method of claim 13, further comprising:
    analyzing the period of time after the end of the activity to determine if the period of time is a recovery period; and
    wherein the heart rate recovery is determined responsive to the period of time after the end of the activity being a recovery period.

18. The method of claim 17 further comprising:
    determining if the period of time after the end of the activity is a recovery period responsive to a length of time between the start of the activity and the end of the activity being greater than a threshold.

19. The method of claim 17 further comprising:
determining if the period of time after the end of the activity is a recovery period responsive to a length of the period of time after the end of the activity, where an activity level is below an activity level threshold, being greater than a duration threshold.

20. The method of claim 17 further comprising:
determining if the period of time after the end of the activity is a recovery period responsive to a number of data points of the heart rate data detected during the period of time, where an activity level is below an activity level threshold, being greater than a data point threshold.

\* \* \* \* \*

UNITED STATES PATENT AND TRADEMARK OFFICE
CERTIFICATE OF CORRECTION

PATENT NO. : 11,638,557 B2
APPLICATION NO. : 16/530130
DATED : May 2, 2023
INVENTOR(S) : Lee et al.

Page 1 of 1

It is certified that error appears in the above-identified patent and that said Letters Patent is hereby corrected as shown below:

In the Claims

In Column 12, Claim 14, Line 38, delete "claim 13" and insert -- claim 13, --, therefor.

In Column 12, Claim 18, Line 63, delete "claim 17" and insert -- claim 17, --, therefor.

In Column 13, Claim 19, Line 1, delete "claim 17" and insert -- claim 17, --, therefor.

In Column 13, Claim 20, Line 7, delete "claim 17" and insert -- claim 17, --, therefor.

Signed and Sealed this
Thirteenth Day of June, 2023

Katherine Kelly Vidal
*Director of the United States Patent and Trademark Office*